US011163311B2

(12) United States Patent
Caussy et al.

(10) Patent No.: US 11,163,311 B2
(45) Date of Patent: Nov. 2, 2021

(54) ROBOTIC EQUIPMENT INCLUDING A MOBILE ROBOT, METHOD FOR RECHARGING A BATTERY OF SUCH MOBILE ROBOT, AND MOBILE ROBOT DOCKING STATION

(71) Applicant: PARTNERING 3.0, Cergy (FR)

(72) Inventors: Ramesh Caussy, La Frette sur Seine (FR); Cyril Hasson, Garches (FR); Antoine Marie Anne Rolland De Rengerve, Cergy (FR); Pierre Jean-Luc Sylvain Delarboulas, Arcueil (FR)

(73) Assignee: PARTNERING 3.0, Cergy (FR)

( * ) Notice: Subject to any disclaimer, the term of this patent is extended or adjusted under 35 U.S.C. 154(b) by 8 days.

(21) Appl. No.: 16/857,500

(22) Filed: Apr. 24, 2020

(65) Prior Publication Data
US 2020/0249688 A1    Aug. 6, 2020

Related U.S. Application Data

(63) Continuation-in-part of application No. 16/065,956, filed as application No. PCT/FR2016/053656 on Dec. 22, 2016, now Pat. No. 10,684,264.

(30) Foreign Application Priority Data

Dec. 24, 2015 (FR) ..................... 15 63341

(51) Int. Cl.
  *G05D 1/00* (2006.01)
  *G05D 1/02* (2020.01)
  *H02J 7/00* (2006.01)
(52) U.S. Cl.
  CPC ......... *G05D 1/0225* (2013.01); *G05D 1/0022* (2013.01); *G05D 1/0276* (2013.01); *H02J 7/00045* (2020.01); *H02J 7/0048* (2020.01)

(58) Field of Classification Search
CPC .. G05D 1/0225; G05D 1/0276; G05D 1/0022; G05D 1/0242; H02J 7/0048; H02J 7/00045; H02J 7/00034; H02J 7/0044
See application file for complete search history.

(56) References Cited

U.S. PATENT DOCUMENTS

| 5,819,008 A | 10/1998 | Asama et al. |
| 6,442,639 B1 | 8/2002 | McElhattan et al. |

(Continued)

FOREIGN PATENT DOCUMENTS

| CA | 2935640 A1 | 7/2015 |
| EP | 1841038 A2 | 10/2007 |
| EP | 2882068 A1 | 6/2015 |
| FR | 2987689 A1 | 9/2013 |
| JP | 2009-061530 A | 3/2009 |

(Continued)

OTHER PUBLICATIONS

U.S. Appl. No. 16/065,956, filed Aug. 8, 2018.

(Continued)

*Primary Examiner* — Ian Jen
(74) *Attorney, Agent, or Firm* — Nixon & Vanderhye (57) ABSTRACT

The invention relates to a system for monitoring air quality in an environment, including at least one mobile robot (20) in the environment, a docking station (10) placed in the environment and including a parking area for receiving the robot, air quality sensors on board the mobile robot, air quality sensors fitted in the docking station, and a calibration manager for collecting measures carried out by at least one air quality sensor on board the mobile robot (20) while the mobile robot is received in the parking area of the docking station (10), and measures carried out at the same time by another air quality sensor fitted in the docking station, of the same type as the on-board air quality sensor.

10 Claims, 10 Drawing Sheets

(56) References Cited

U.S. PATENT DOCUMENTS

| | | |
|---|---|---|
| 10,048,695 B2 | 8/2018 | Hoshino |
| 2006/0190133 A1 | 8/2006 | Konandreas et al. |
| 2009/0044370 A1 | 2/2009 | Won et al. |
| 2009/0315501 A1 | 12/2009 | Li et al. |
| 2012/0226381 A1 | 9/2012 | Abramson et al. |
| 2013/0074575 A1 | 3/2013 | Duric et al. |
| 2013/0110322 A1 | 5/2013 | Jaegenstedt et al. |
| 2015/0042273 A1 | 2/2015 | Laupin-Villemus et al. |
| 2015/0057800 A1 | 2/2015 | Cohen et al. |
| 2016/0272291 A1 | 9/2016 | Outa et al. |
| 2016/0374528 A1 | 12/2016 | Morin et al. |
| 2017/0164800 A1 | 6/2017 | Arakawa |
| 2017/0364087 A1 | 12/2017 | Tang et al. |
| 2018/0035606 A1 | 2/2018 | Burdoucci |
| 2018/0088592 A1 | 3/2018 | Gildner et al. |
| 2018/0177369 A1 | 6/2018 | Morin et al. |
| 2019/0011413 A1* | 1/2019 | Caussy ............... G01N 33/0031 |

FOREIGN PATENT DOCUMENTS

| | | |
|---|---|---|
| WO | 00/78204 A2 | 12/2000 |
| WO | 2013/119942 A1 | 8/2013 |
| WO | 2015/063119 A1 | 5/2015 |

OTHER PUBLICATIONS

PCT Search Report, dated Feb. 17, 2017, from corresponding PCT application No. PCT/FR2016/053656.

FR Search Report, dated Aug. 5, 2016, from corresponding FR application No. 1563341.

PCT Search Report, dated Apr. 7, 2017, from corresponding PCT application No. PCT/FR2016/053655.

Kim et al., "Development of Docketing System for Mobile Robots Using Cheap Infrared Sensors", 1st International Conference on Sensing Technology, 2005, pp. 287-291, XP055299565.

* cited by examiner

ROBOTIC EQUIPMENT INCLUDING A MOBILE ROBOT, METHOD FOR RECHARGING A BATTERY OF SUCH MOBILE ROBOT, AND MOBILE ROBOT DOCKING STATION

The present invention relates to a system comprising one or more mobile robots and one or more associated docking stations.

BACKGROUND

Service robotics is a growing field. Mobile robots can be dedicated to various functions such as floor cleaning (for example US 2006/190133 A1), transporting loads (for example WO 2013/119942 A1), patrolling warehouses (for example FR 2,987,689 A1), monitoring air quality in closed environments (for example WO 2015/063119 A1), etc.

Mobile robots are associated with docking stations. The primary role of the docking stations is to provide energy. This is generally electric power, the robot being equipped with a battery that is recharged when it docks with the station. Usually each robot has its own docking station where it is parked when not carrying out its tasks, its recharging occurring during that time.

The docking station has a charge management system that tracks the charge of the robot from start to full recharge.

The docking station often has a robot guidance feature, allowing the robot to reach the proper position in the station to begin charging. Various devices exist for such guidance. The most common are based on a system of infrared light emitting diodes (LED) enabling the robot to determine the direction to take from its position relative to the docking station. For example, see US 2015/0057800 A1 concerning a docking station for a robot vacuum cleaner.

Sometimes there is also a physical docking guidance system at the station. Such a physical guidance system, however, poses problems which restrict the design of the robot/docking station pair.

More generally, it seems desirable to improve robustness in guiding the robot to the correct position relative to the docking station, in other words to improve the success rate of the procedure of positioning the robot at the station.

Existing docking stations usually only offer to docked mobile robots an energy recharging service, although robots may have other requirements depending on the services they provide.

Service robotics are enabling the introduction of new types of robots into the workplace and the home. These have different shapes, sizes, and requirements for energy and continuity of supply. These emerging requirements and the need to integrate large groups of robots that potentially recharge on the same station generally have not been considered in the design of existing docking stations. This hinders growth in service robotics and in the multitude of services that can result from new relationships between the station and robots of different capabilities.

To facilitate deployment of mobile robot fleets at a given site, the design of the docking station should enable it to accommodate different robots, including robots of different sizes. Deployment will also be facilitated if the same robot can engage with different docking stations.

Another aspect to consider is the safety of the charge management procedures. EP 1841038 A2 describes a charging station having a safety feature to prevent short circuits when a metal object touches its charge contactors. This type of measure may be insufficient, however. If robots of different types are likely to be accepted by the same station, charge features suitable for each of them must be offered, while ensuring that the charging process takes place under acceptable physical conditions and preventing the station from supplying electric power in the absence of an authorized and identified robot.

An object of the present invention is to address at least some of the above needs.

SUMMARY

A docking station for a mobile robot is proposed, comprising:
  a robot parking area;
  sources of attracting beams arranged around the parking area in order to emit attracting
  beams within a robot approach region; and
  sources of repelling beams arranged on either side of the parking area in order to emit,
  outside the approach region, repelling beams of shorter range than the attracting beams.

These arrangements ensure that the robot can approach the station from the appropriate directions, defined by the attracting beams, while avoiding collisions with the station due to approaching from inappropriate directions defined by the repelling beams. Typically, the attracting beams are emitted in front of the station, while the repelling beams are emitted laterally.

In one embodiment, the sources of attracting beams are arranged such that the attracting beams are emitted in directions which intersect at a fixed point of the parking area. One of the sources of attracting beams may be arranged to emit an attracting beam having priority feature, so that a mobile robot executes a final path between the fixed point and a docking position in the parking area. This method ensures accurate positioning of the robot docked in the docking station without the need for mechanical guidance means.

In one particular configuration of the docking station, the sources of attracting beams are arranged to emit an attracting beam in a first direction and two attracting beams in two respective directions which are symmetrically oriented with respect to the first direction. Sources of repelling beams are arranged on each side of the parking area in order to emit two attracting beams outside of the approach region in two respective directions which are symmetrically oriented with respect to the first direction.

The repelling beams, which are shorter-range than the attracting beams, may have a wider beamwidth than the attracting beams. Guidance toward a specific direction is achieved by attracting beams which are relatively narrow, while the directions of approach to be avoided are marked by wider repelling beams.

One embodiment of the docking station further comprises:
  a beam source activation controller for activating the beam sources alternately according to an activation time cycle; and
  a beacon signal source for emitting a beacon signal around the docking station, indicating a current phase of the activation time cycle.

The activation time cycle may comprise a step of emitting repelling beams and, for each source of attracting beams, a step of emitting the attracting beam from said source. Detection of the beacon signal by a robot approaching the docking station allows it to identify which beam it is currently receiving (attracting or repelling). It can then decide which maneuver to make in order to come and connect to the docking station.

The activation time cycle may also comprise a step of no beam emission during which the ambient noise is measured. From this measurement, the infrared signal detection criteria can be adjusted to reflect the signal-to-noise ratio, which is variable. This allows determining if what the infrared sensors are detecting corresponds to a useful signal or to ambient noise to be ignored.

In one embodiment, the beacon signal further indicates an identifier of the docking station. By decoding the beacon signal, a mobile robot can then ensure that it is approaching a docking station appearing in a list of authorized stations that it has stored.

When the docking station provides the basic function of recharging a mobile robot, it comprises a pair of contactors typically arranged in the parking area. It may further comprise a communication interface for communicating with a mobile robot docked in the parking area, controlled to transmit a mobile robot identification request in response to voltage detected at the contactors. The communication interface with the mobile robot, when there is no contact, generally also operates while the robot is approaching and has not yet docked in the docking station.

Advantageously, a recharging controller is configured to provide charge power to the contactors if a mobile robot identifier authorized for the station is received via the communication interface, after a request for identification is transmitted.

A docking station according to the invention may further be equipped with a wireless communication access point for mobile robots, and a network interface for transmitting data obtained by the mobile robots to a data collection server.

The network interface may be configured to retrieve updated files for the embedded software of the mobile robots, the updated files being transmitted to the mobile robots via the wireless communication access point. The station itself can be updated by this process.

Independently of the above features or in combination therewith, a system is proposed for monitoring air quality in at least one environment, comprising:
  at least one mobile robot in the environment;
  a docking station placed in the environment and having a parking area for receiving the robot;
  air quality sensors on board the mobile robot;
  air quality sensors installed in the docking station; and
  a calibration controller for collecting measurements made by at least a first air quality sensor on board the mobile robot, while the mobile robot is docked in the parking area of the docking station, and for collecting measurements made at the same time by a second air quality sensor installed in the docking station and of the same type as said first air quality sensor.

This system makes use of the time the robots must spend in the docking stations, usually for recharging, to verify the measurements made, for the same air surrounding the docking station, by the sensors on board the robots and those permanently installed in the docking station. This considerably reduces the maintenance operations required to verify proper calibration of the sensors.

The calibration controller of the system can be configured to transmit to the mobile robot drift observed in the collected measurements correction parameters.

This calibration controller may be more or less remote. However, it is wise to install it at least in part in the docking station, with another part in the robots. The system may then further comprise a collection server communicating with the calibration controller to process the collected measurements and provide drift observed in the collected measurements correction parameters. The collection server can then determine the drift correction parameters in order to calibrate the first air quality sensor on board the mobile robot, relative to the second air quality sensor installed in the docking station. When the docking station is able to successively receive a plurality of mobile robots in the parking area, the collection server may be configured to process measurements made by first air quality sensors of the same type on board their respective mobile robots while said mobile robots are successively received in the parking area, in comparison to measurements made at the same time by the second air quality sensor installed in the docking station and of the same type as said first air quality sensors. Another interesting possibility is for the processing of measurements by the collection server to include an analysis of the differences observed between the measurements made by the first air quality sensors and those made at the same time by the second air quality sensor, and triggering an alert when the analyzed differences meet a predefined alert condition. When the system has multiple docking stations, the collection server is advantageously configured to communicate with calibration controllers installed at least in part in a plurality of docking stations.

According to another aspect, a mobile robot docking station comprises:
  a parking area for receiving at least one mobile robot in an environment where the docking station is placed;
  reference sensors of the same type as the air quality sensors on board a mobile robot;
  and
  a calibration controller to collect air quality measurements made by at least one air quality sensor on board a mobile robot while said mobile robot is received in the parking area, and measurements made at the same time by a reference sensor of the docking station.

The docking station may further comprise a network interface for transmitting data obtained by the mobile robot to a collection server, the calibration controller being configured to transmit to the collection server, via the network interface, the air quality measurements made by the air quality sensor on board the mobile robot while said mobile robot is received in the parking area, and the measurements made at the same time by a reference sensor of the docking station. The calibration controller may be configured to transmit to the mobile robot drift observed in the collected measurements correction parameters.

Independently of the foregoing features, or in combination therewith, a method is proposed for recharging the battery of a mobile robot in an environment, using a docking station located in the environment. The method comprises:
  moving the mobile robot to the docking station;
  emitting a wireless beacon signal from the docking station;
  upon detection of the beacon signal by the mobile robot, the mobile robot communicates with the docking station such that the docking station retrieves information concerning the mobile robot; and
  initiating the recharging of the battery of the mobile robot in a manner that is dependent on the retrieved information concerning the mobile robot.

Establishing an exchange of information between the docking station and the newly arrived robot allows a secure process for charging the robot, and/or for adapting the characteristics to the type of robot in question. The method thus allows managing the charging of a robot fleet having different characteristics or identities, using one or more docking stations.

In one embodiment of the method, the information retrieved by the docking station concerning the mobile robot comprises an identifier of the mobile robot, the charging beginning if the mobile robot identifier included in the retrieved information corresponds to an identifier in a list of authorized robots stored in the docking station.

In particular, the charge power can be selected based on the information retrieved by the docking station concerning the mobile robot.

One advantageous embodiment of the recharging method comprises:
  in response to detection of the beacon signal by the mobile robot, presenting a voltage at an electric power receiving interface comprised in the mobile robot for recharging the battery, for example a pair of charge terminals accessible from outside the robot;
  in response to detection of the voltage at an electric power delivery interface comprised in the docking station, for example a pair of contactors accessible from outside the station, transmitting an identification request from the docking station to the mobile robot; and
  transmitting information concerning the mobile robot to the docking station in response to the identification request.

Typically, the beacon signal carries an identifier of the docking station. One can then ensure that the mobile robot is prevented from transmitting information concerning the mobile robot when the docking station identifier received in the detected beacon signal does not match any identifier in a list of authorized docking stations stored in the mobile robot.

While recharging the battery of the mobile robot, the method may comprise:
  monitoring parameters such as at least the battery voltage of the mobile robot, the charge current delivered to the mobile robot, and the temperature of a charging circuit of the docking station; and
  stopping the charge power when the recharging conditions are no longer met.

In another aspect, the robotic equipment comprises:
  at least one mobile robot, the mobile robot comprising:
    a battery;
    a motor system powered by the battery to move the mobile robot within an environment;
    an electric power receiving interface for recharging the battery; and
    a first communication interface; and
  at least one docking station to be placed in the environment, the docking station comprising:
    a parking area for receiving at least one mobile robot;
    a source of electric power;
    an electric power delivery interface for cooperating with the electric power receiving interface of a mobile robot received in the parking area and charging the battery of said mobile robot from the source of electric power;
    a source of wireless beacon signal for transmitting a beacon signal around the docking station;
    a second communication interface for cooperating with the first communication interface of the mobile robot and retrieving information concerning the mobile robot received in the parking area after emission of the beacon signal by the source of the beacon signal; and
    a recharging controller for recharging the battery of the mobile robot received in the parking area in a manner that is dependent on the information concerning the mobile robot received via the second communication interface.

In another aspect, a mobile robot docking station comprises:
  a parking area for receiving at least one mobile robot in an environment where the docking station is placed;
  a source of electric power;
  an electric power delivery interface coupled to the source of electric power in order to recharge a battery of a mobile robot received in the parking area;
  a source of wireless beacon signal for transmitting a beacon signal around the docking station;
  a communication interface for communicating with the mobile robot received in the parking area in order to retrieve information concerning said mobile robot after transmission of the beacon signal by the source of the beacon signal; and
  a recharging controller for recharging the battery of the mobile robot received in the parking area in a manner that is dependent on the information concerning said mobile robot retrieved via the communication interface.

According to another aspect, a mobile robot comprises:
  a battery;
  a motor system powered by the battery to move the mobile robot within an environment;
  an electric power receiving interface for recharging the battery, the power coming from a docking station located in the environment;
  a wireless beacon signal detector for detecting a beacon from the docking station;
  an interface for communicating with the docking station; and
  a controller configured to:
    in response to detection of the beacon signal, present a voltage at the electric power receiving interface; and
    in response to receiving an identification request via the interface for communicating with the docking station after presenting a voltage to the electric power receiving interface, transmitting identification information concerning the mobile robot to the docking station.

When the beacon signal carries an identifier of the docking station, the controller can be configured not to transmit the mobile robot identification information when the docking station identifier received in the detected beacon signal does not match any identifier in a list of authorized docking stations stored in the mobile robot.

BRIEF DESCRIPTION OF DRAWINGS

Other features and advantages of the invention will be apparent from the following description of an exemplary non-limiting embodiment, with reference to the accompanying drawings in which.

DESCRIPTION OF EMBODIMENTS

Figure 1:
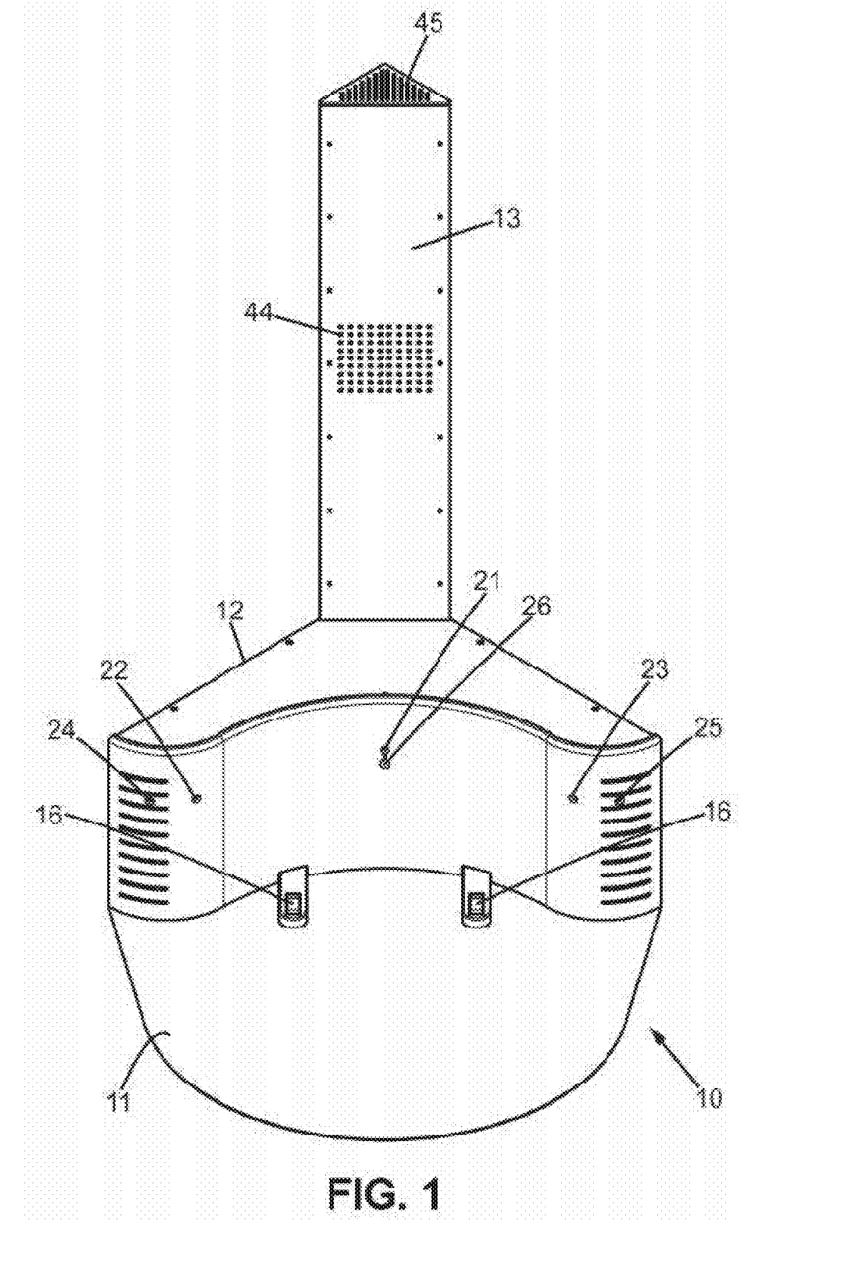
FIG. 1 is a diagram of an exemplary docking station having features of the invention, in plan view.
Figure 2:
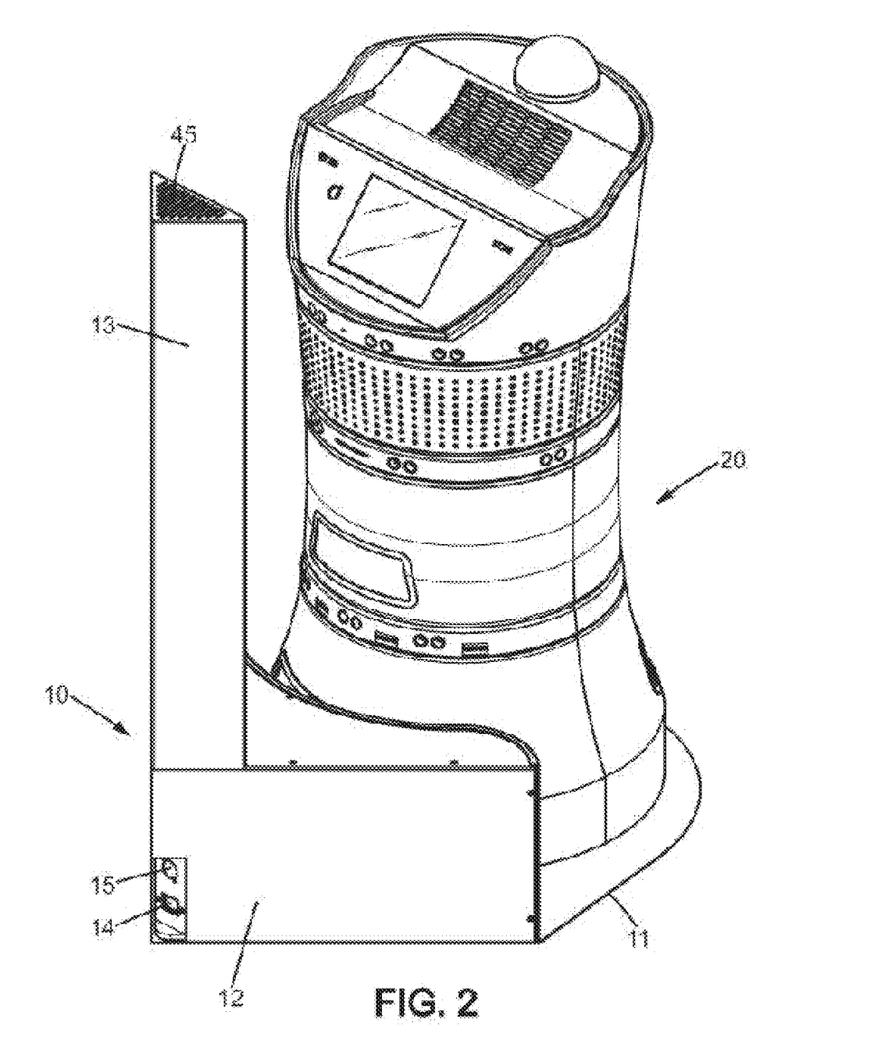
FIG. 2 is a perspective diagram of the docking station of FIG. 1, with a mobile robot docked.

The docking station 10 shown by way of example in FIGS. 1 and 2 rests on the ground by means of a plate-shaped base 11 which defines a parking area for a mobile robot 20. It further comprises a housing 12 which contains a number of components described below, and a pillar 13 at the back of the station relative to the robot parking area.

In this example, the docking station 10 is designed to be placed in a corner of a room. The rear side of the housing 11 and pillar 12 form a right-angle that can be fit into the corner, and the structure of the docking station is generally symmetrical relative to the bisector of the right angle. A connector is provided at the rear of the housing 12, with a plug 14 to supply electricity to the station 15 and a network port.

The front of the housing 12 has a concave profile to enable receiving a mobile robot 20 having a generally circular base within the parking area. The opening in the front of the housing may be designed to accommodate robots 20 of different diameters or shapes in the parking area.

In the front of the housing 12, the base 11 has two contactors 16 which cooperate with charging contacts located on the underside of the mobile robots 20. The contactors 16 are connected to electric components housed in the housing 12.

Sources of guide beams, typically infrared LEDs 21-25, are placed on the front of the housing 12 to assist the robot 20 when it approaches the station 10. An infrared transceiver 26 is also provided to allow short-range communication between the docking station 10 and a robot 20 which is docked.

Figure 3:
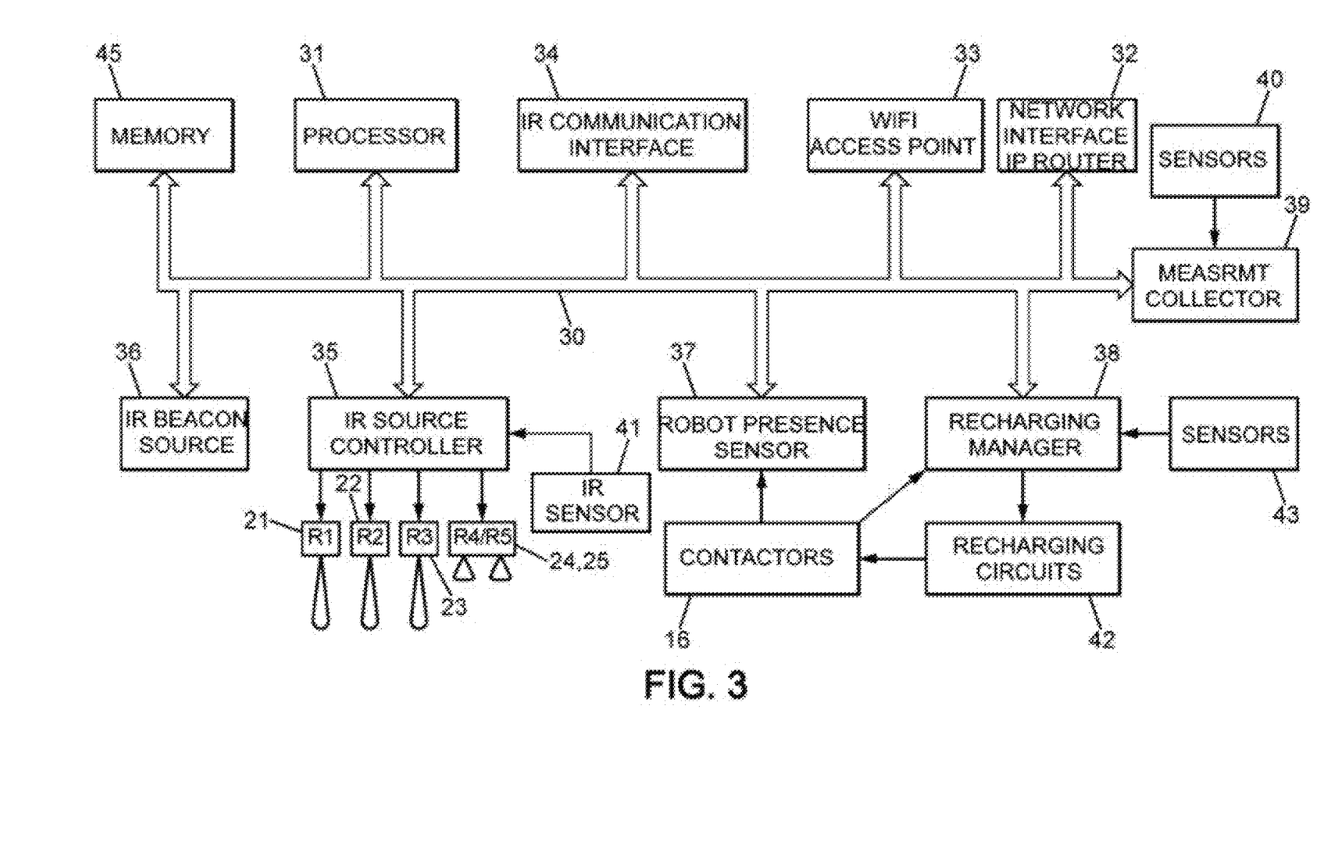
FIG. 3 is a block diagram of units which are part of a docking station in an exemplary architecture suitable for implementing the invention.

FIG. 3 illustrates the electronic components that can be found inside the docking station 10. Of course, the illustrated architecture, which is organized around a bus 30, is a simple non-limiting example. In this example, the bus 30 is controlled by a processor 31 accommodated in the housing 12, which supervises the operation of the various components by means of appropriate software modules. Here these components include:

- a memory 45 associated with the processor 31;
- a network interface 32, for example Ethernet, coupled with an IP router, which enables connecting the docking station 10 to the network of a company using a fleet of mobile robots, and/or to the Internet, via the network port 15;
- a WiFi access point 33 providing a wireless communication interface with the mobile robots operating in the environment where the docking station is installed;
- an infrared communication interface 34, for example IrDA;
- a controller 35 for the infrared LEDs 21-25;
- an omnidirectional source, such as an infrared LED 36, which emits a beacon signal at or near the docking station 10;
- a sensor 37 for detecting the presence of a robot docked in the docking station, which cooperates with the exposed contactors 16 in the parking area;
- a recharging controller 38 which oversees the process of recharging the mobile robots;
- a component 39 which collects the measurements made by a set of reference sensors 40 equipping the docking station 10.

Note that some of the components 32-39 shown separately in FIG. 3 may possibly be implemented, in all or part of their functionality, as software modules executed by the processor 31 or one of its devices.

Figure 4:
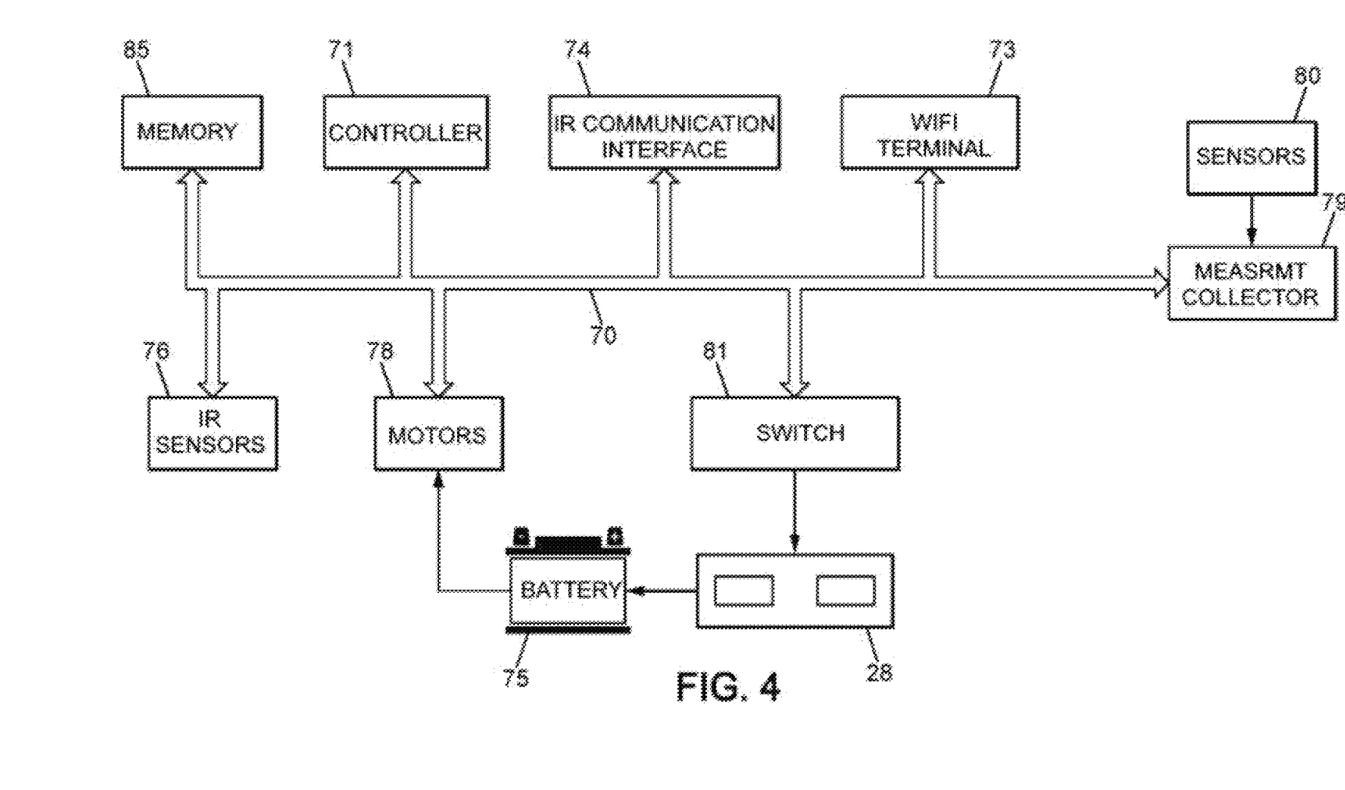
FIG. 4 is a block diagram of units which are part of a mobile robot in an exemplary architecture suitable for implementing the invention.

FIG. 4 illustrates electronic components that may be found inside a robot 20. Of course, the specified architecture, which is organized around a bus 70, is a simple non-limiting example. In this example, the bus 70 is controlled by a controller 71, such as a microprocessor or microcontroller, embedded in the robot 20, which oversees the operation of the various components by means of appropriate software modules. These components include here:

- a memory 85 associated with the controller 71;
- a WiFi terminal 73 for wireless communication with the access point 33 of a docking station 10, or with another WiFi access point;
- an infrared communication interface 34, for example IrDA, for short-range communication with the infrared interface 34 of a docking station 10;
- a motor system 78 comprising one or more motors arranged to move the robot 20 autonomously with power supplied from the battery 75 of the robot;
- a plurality of infrared sensors 76 for detecting the guide beams emitted by the sources 21-25 of a docking station 10 and the beacon signal emitted by the source 36 of such a station;
- a switch 81 which, when so instructed by the controller 71, presents the voltage 75 from the battery to a pair of charging contacts 28 which are accessible from outside the robot, for example under its chassis, for recharging the battery 75; and
- a component 79 which collects the measurements made by a set of sensors 80 on board the robot 20.

One will also note that some of the components 73, 74, 79, 81 shown separately in FIG. 4 may possibly be implemented, in all or part of their functionality, as software modules executed by the controller 71 or one of its peripherals.

Figure 5:
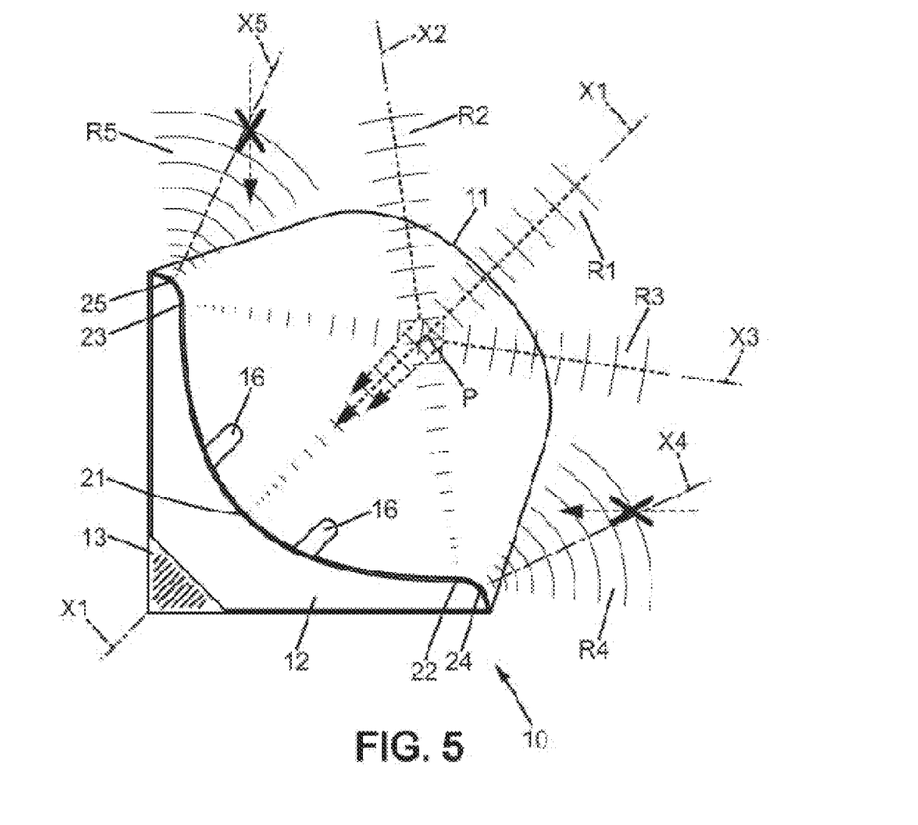
FIG. 5 is a schematic top view showing attracting beams and repelling beams in an exemplary embodiment.

FIG. 5 shows an exemplary geometry of the attracting and repelling beams emitted by the infrared LEDs 21-25 of the docking station 10.

LED 21 emits an attracting beam R1 oriented in the horizontal direction X1 and passing through the plane of symmetry of the docking station 10.

LEDs 22, 23, arranged at the sides of the front face of the housing 12, emit respective attracting beams R2, R3 in directions X2, X3 arranged symmetrically relative to direction X1. Directions X1, X2 and X3 intersect at a point P located within the parking area of the docking station. In the example shown, the angle formed between directions X1, X2 and between directions X1, X3 is about 50°.

Infrared LEDs 24, 25 are arranged laterally on the front face of the docking station 10, near the corners thereof. They emit repelling beams R4, R5 of shorter range than the attracting beams R1, R2, R3 (for example 15 to 30 cm compared to 50 to 100 cm). As shown in FIG. 5, the beamwidth of the repelling beams R4, R5 is preferably greater than that of the attracting beams R1, R2, R3 (for example about 60° compared to) 15°. The angle formed between directions X1, X4 and between directions X1, X5 is for example from 10 to 20°.

When it needs to return to the docking station 10 in order to charge its battery 75 or for other services, a mobile robot 20 can no longer rely on its obstacle avoidance systems to determine its path. Otherwise it would never reach the docking position at the docking station, which is the position where its charging contacts 28 on its underside are against the contactors 16. The robot must therefore be guided from the outside, which is the role of the infrared sources 21-25.

The mobile robots 20 are equipped with infrared sensors 76 at the height of the LEDs 21-25. When one of the attracting beams R1-R3 is sensed by a mobile robot, the controller 71 determines the direction of origin of the beam and controls the motor system 78 so that the robot moves towards the LED from which the beam was emitted. In contrast, if it is a repelling beam R4, R5, the motor system 78 is controlled so that the robot moves away from the LED where it originated. The distinction between attracting and repelling beams is made by the robot 20 by receiving the beacon signal emitted by the LED 36 of the docking station 10, the beams being emitted sequentially according to an activation cycle controlled by the controller 35.

The LEDs 21-25 are successively activated by the controller 35 in a cycle whose frequency is for example 20 Hz. The activation cycle is composed of several steps during which the LEDs 21-25 are activated in turns. At the same time, a specific encoded signal is emitted by the beacon LED 36. This activation cycle guides the robot 20 to the station 10 while managing priorities between the beams, measuring the ambient infrared noise and having the robot identify the station.

Figure 6A:
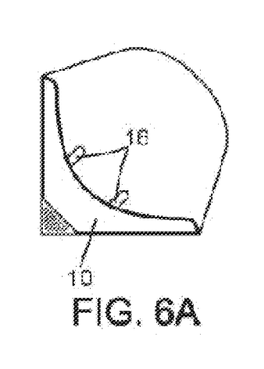
FIGS. 6A-E are diagrams illustrating various steps of an exemplary activation cycle for the sources of attracting and repelling beams.
Figure 6B:
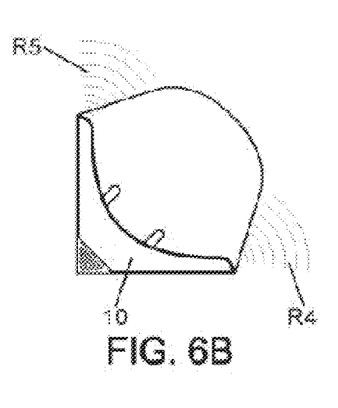
Figure 6C:
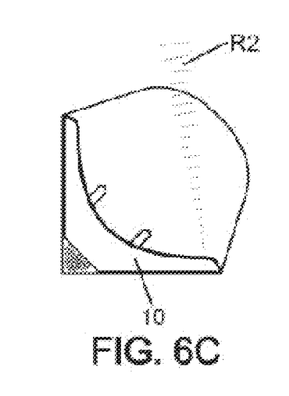
Figure 6D:
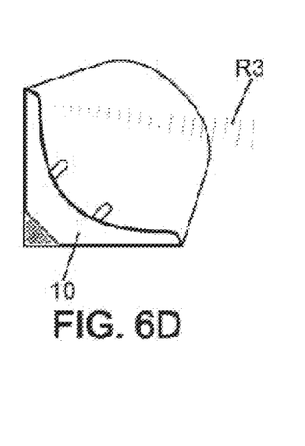
Figure 6E:
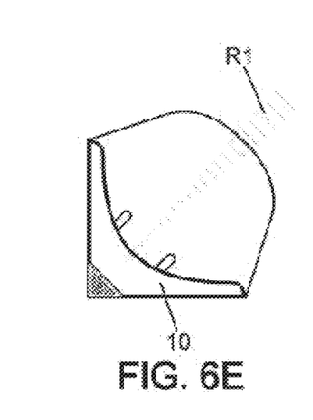

The LED beacon 36 thus emits omnidirectional infrared signal packets having a header which includes an identifier of the docking station 10, and a packet body which provides codes indicating the current steps of the activation cycle. There are for example five steps of the same duration in the activation cycle, illustrated by FIGS. 6A-E:
  a first step (FIG. 6A) in which none of the LEDs 21-25 is supplied power, the docking station being able to measure the ambient infrared noise by means of an infrared sensor 41 associated with the controller 35 (FIG. 3);
  a second step (FIG. 6B) in which only LEDs 24, 25 are activated to emit repelling beams R4, R5;
  a third step (FIG. 6C) in which only LED 22 is activated to emit attracting beam R2;
  a fourth step (FIG. 6D) in which only the opposite LED 23 is activated to emit attracting beam R3; and
  a fifth step (FIG. 6E) in which only the central LED 21 is activated to emit attracting beam R1.

When a robot detects one of the infrared beams R1-R5 in the vicinity of the docking station 10, it reads the code transmitted in the beacon signal to determine which beam is concerned. It can then orient itself and move towards the parking area of the docking station. When the activation cycle is in the first step (FIG. 6A), the robot can also measure the ambient infrared noise using its sensors 76.

While being guided, the robot (at least its infrared receiver) draws near to the intersection point P of beams R1-R3 (FIG. 5). The ambiguity concerning the direction the robot must follow to complete the docking procedure is removed by means of codes transmitted by the LED beacon: the robot is programmed to head towards the source 21 of beam R1 detected during the fifth step of the cycle illustrated in FIGS. 6A-E, which brings it to the docking position. In other words, beam R1 has a priority property which, in the example considered here, is expressed in the codes emitted by the LED beacon 36.

Measurement of the ambient infrared noise by sensors 41 and/or 76 during the first step of the activation cycle allows controller 35 and/or 71 to take into account the signal-to-noise ratio. The higher the measured ambient noise is, the stricter the selected criteria used to separate a signal from the ambient noise is chosen. This method prevents the guide signals from being altered by environmental disturbances such as variations in brightness or wave pollution.

Each mobile robot 20 has a predefined list of docking stations with which it is allowed to dock, stored in its memory 85. The identifier of the docking station 10 which it is approaching, broadcast in the beacon signal emitted by LED 36, allows the robot to check whether it is authorized for that docking station.

Alternatively, identification of the docking station 10 by a mobile robot 20 can be performed using the association identifier broadcast on the IEEE 802.11 beacon channel by the WiFi access point 33 of the station 10.

It is appropriate for the docking stations 10 also to be able to securely identify the robots 20 that come to them.

The robot presence sensor 37 and the infrared communication interface 34 may be used for this, according to a procedure illustrated in FIGS. 7A-E.

Figure 7A:
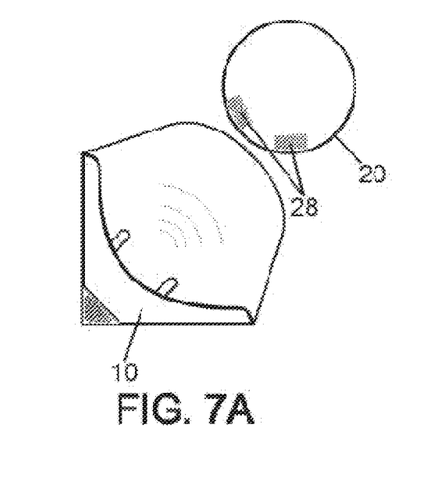
FIGS. 7A-E are diagrams illustrating various steps of an exemplary process in the approach and identification of a mobile robot to the docking station.
Figure 7B:
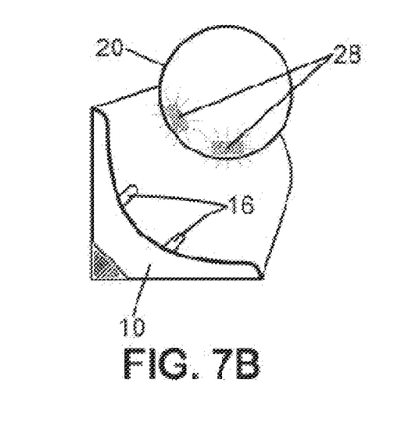
Figure 7C:
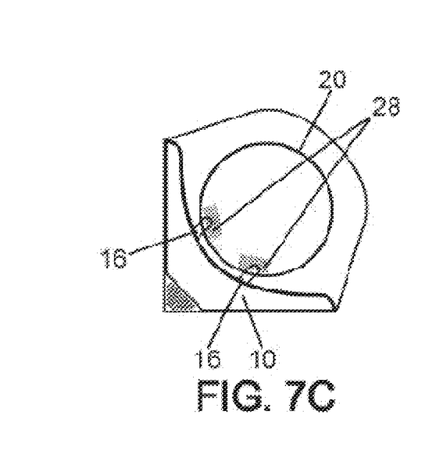

FIG. 7A shows a mobile robot 20 which is approaching a docking station 10. The detection of a guide signal from a station authorized for a given robot, meaning one of beams R1-R3 and the beacon signal emitted by the LED 36, allows the robot to verify that the station is indeed authorized and then to present the voltage from the battery to the charging contacts 28 located under its chassis (FIG. 7B). Thus, once a robot is properly positioned in a station (FIG. 7C), the station detects it by reading on its contactors 16 the residual voltage from the battery of the robot. This is the role of the robot presence sensor 37 coupled to the contactors 16.

Figure 7D:
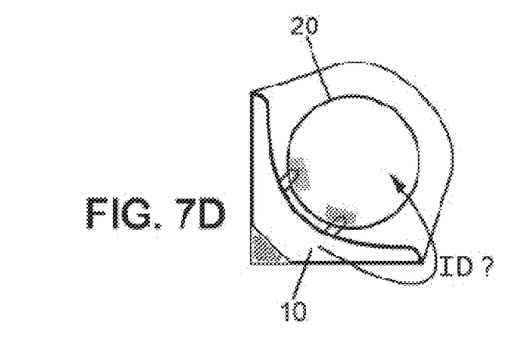

In order to have a secure procedure to initiate charging, the station 10 then begins a dialog with the robot 20 via infrared communication. The station 10 first checks that the voltage it detects is indeed the voltage of the robot. For this purpose, the station 10 requests the robot 20 to identify itself, via the infrared interface 34 (FIG. 7D).

If the reply sent by the robot 20 (FIG. 7E) identifies it correctly, meaning if the robot identifier returned appears in a list of identifiers authorized for the docking station 10, stored in the memory 45 of the station, the station makes available all of its capabilities (charging and other services) to the robot 20. In addition, it records the information that the robot in question is indeed docked at the station 10, making this information accessible to the robot fleet controller via the network interface 32.

Figure 7E:
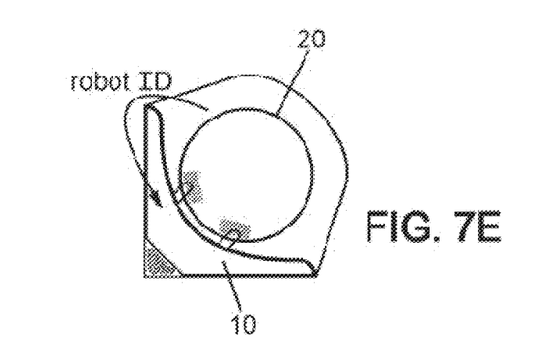

If the station 10 does not receive a response or if the robot returns an invalid or unauthorized identifier (7E), the station does not supply charge current nor any of the other services it offers.

The method described above, of dual identification of docking stations by robots and of robots by docking stations, allows simple and flexible management of the operation of a robot fleet having access to a plurality of docking stations.

The pairing between robots and docking stations, meaning the storage of lists of robots and stations authorized to work together, can be done when deploying robots and stations at an operating site. A simple way to do this is to present a robot 20 to a station 10 which it will be authorized to work with and to activate a coupling procedure by means of a button provided on the robot or the station, this procedure consisting of registering the identifier of the robot in the memory 45 of the docking station and that of the docking station in the memory 85 of the robot. Another way to pair consists of providing lists of robots and the stations with which they can connect by means of a computer interface available to the fleet controller (tablet or computer) and then transmitting the appropriate lists to the docking stations via their network interfaces 32, and to the robots via the WiFi network.

Managing the recharging process for high capacity robots advantageously includes a number of measures to ensure greater reliability and better safety. It may be that the docking station 10 receives robots 20 having batteries of different electrical properties. It must then be provided with charging circuitry 42 able to deliver different voltage/current properties. Due to the identification of the presenting robots, the recharging controller 38 of the station can select the appropriate mode of operation of the recharging circuits 42 for each robot.

As the current involved can be significant, it is critical to have a safe charging process. When the voltage exceeds 5 volts and the current several amperes (for example 25V/7A or more), the safety constraints are more strict.

This is why it is appropriate for the recharging controller 38 to control the recharging circuits 42 (transformers, switches, and associated electronics) so that, by default, the charge voltage is not available on the contactors 16 of the docking station 10. This eliminates the risk of an accidental short-circuit. The recharging procedure entails the robot identifying itself (FIGS. 7D-E) and presenting the residual voltage from its battery 75 to its charging contacts 28. It is under these preconditions that charge power is supplied at the contactors 16 of the station. The battery of the robot 20 can then begin recharging.

Figure 8:
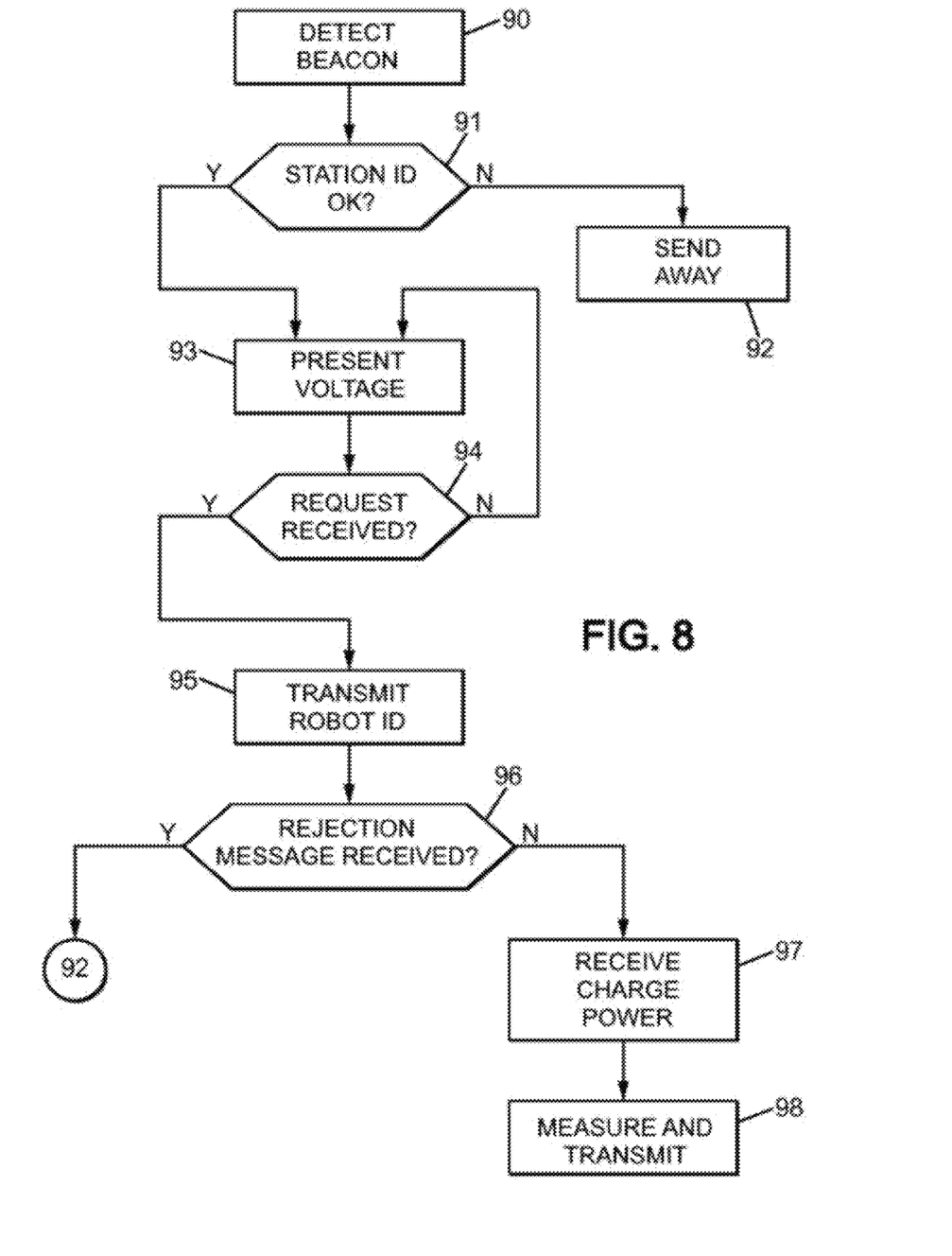
FIGS. 8 and 9 are flowcharts illustrating steps implemented respectively by a mobile robot and a docking station according to an exemplary method for recharging the battery of the robot.
Figure 9:
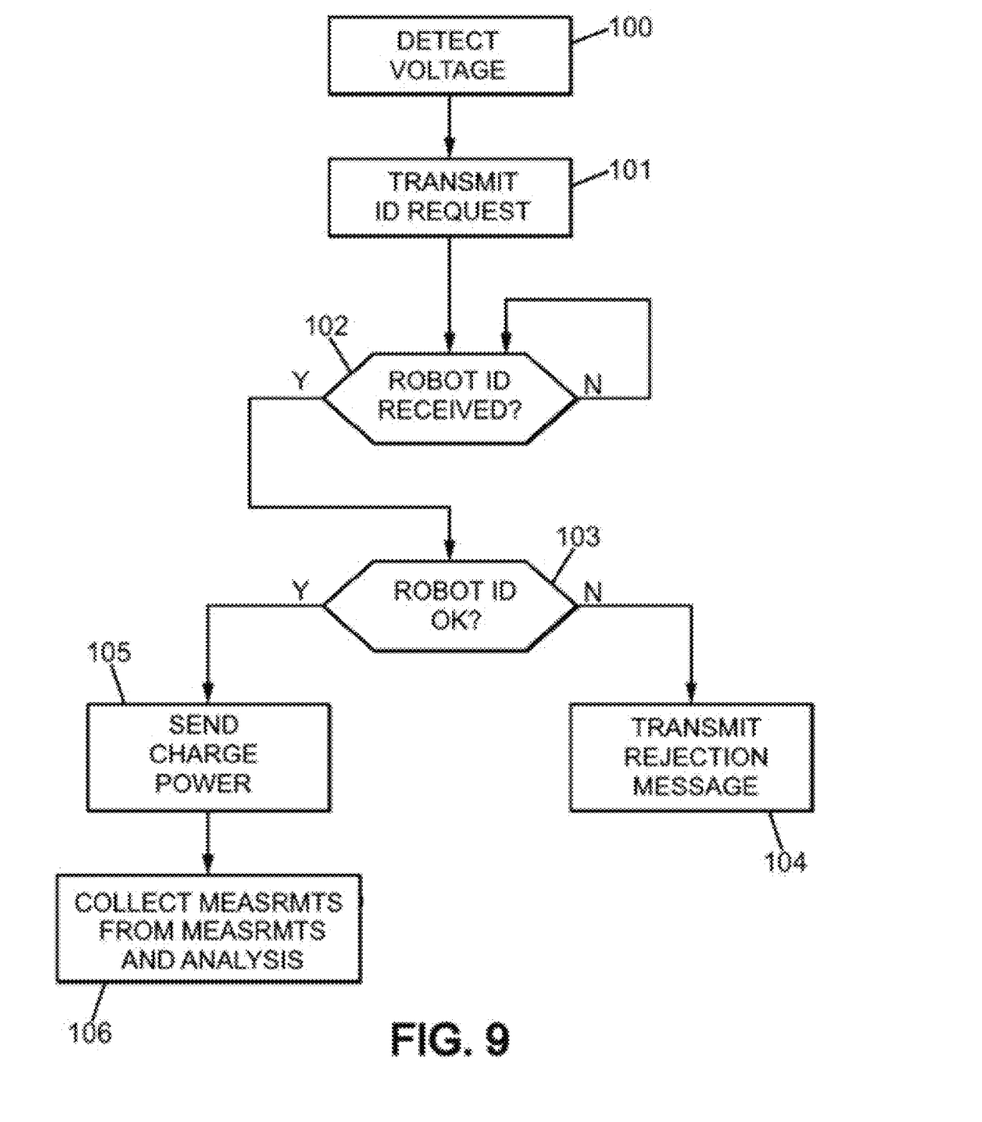

Managing the approach of the robot for recharging purposes can be performed according to the procedures illustrated in FIG. 8 concerning the mobile robot (controller 71) and in FIG. 9 concerning the docking station (processor 31 and/or recharging controller 38).

In response to detection of a beacon signal by an infrared sensor 76 of the robot (step 90), the controller 71 first checks whether the identifier of the docking station carried by the beacon signal appears in the list of authorized stations available in the memory 85 of the robot (test 91). If it is an unauthorized identifier, the controller 71 controls the motor system 78 so that the robot 20 moves away from the unsuitable docking station 10 (step 92).

If the identifier received in the beacon signal is that of a docking station authorized for the robot, the controller 71 controls the switch 81 so that the voltage from the battery 75 is present on the charging contacts 28 of the robot (step 93). Then the robot waits to receive a request for identification from the docking station (test 94). Upon receipt of this request, the controller 71 controls the infrared interface 74 so that the identifier of the robot 20 is transmitted to the docking station 10 in step 95.

After transmitting its identifier, the controller 71 of the robot examines whether a rejection message is received on the infrared interface 74 from the docking station 10 (test 96). In case of rejection by the host station, step 92 is executed so that the robot moves away from the station. If the robot is accepted by the docking station, it starts to receive the power delivered by the docking station at its charging contacts 28 in order to recharge its battery 75 (step 97).

As for the docking station 10, the procedure illustrated in FIG. 9 is triggered by the detection 100 of voltage at the contactors 16 placed in the parking area, by the sensor 37. In response to detecting voltage at the contactors 16, the processor 31 controls the infrared interface 34 so that the request for identification from the robot 20 which has reached the parking area is transmitted (step 101).

Then the docking station 10 waits to receive a message supplying the identification of the mobile robot (test 102). Upon receipt of this message, the processor 31 verifies (test 103) that the received identifier appears in the list of robots authorized for the docking station, stored in memory 45. If it is an unauthorized identifier, the processor 31 orders the transmission, by the infrared interface 34, of a rejection message for the robot that has reached the parking area. If the mobile robot 20 is authorized for the docking station 10, the station's processor 31 controls the recharging controller 38 so that charge power for the robot battery is sent to the contactors 16.

Once charging the robot battery 75 has been initiated, measurements are continuously collected by means of the sensors 43 equipping the docking station:
  voltage of the robot battery 75 measured at the terminals of the contactors 16;
  charge current amperage; and
  temperature of the charge circuits.

These measurements, to which can be added the temperature of the robot battery 75 as measured by the robot and transmitted to the station via the WiFi or infrared interface (step 98 of FIG. 8), are used to define the charging status (no robot present, charging initialization, charging, end of charging) but also to define ranges of measurements defining normal operation.

The measurements made by the docking station 10 and those received from the robot 20 during recharging are analyzed by the processor 31 in step 106 represented in FIG. 9. If one of the indicators lies outside the normal operating range, an alert is triggered by the recharging controller 38. The alert leads the recharging controller 38 to automatically stop the charge voltage at the contactors 16. One can thus detect and terminate any malfunction, whether or not it is potentially dangerous. If an anomaly is detected, a warning message is issued by the docking station 10 via the Ethernet in order to inform the robot fleet manager.

Other interesting features of the docking station 10 described here as an example relate to the sensors 80 on board the mobile robots 20. In particular, in the application where a set of robots is used to carry out air quality measurements in a closed environment in which the docking station is also located, the robots have embedded sensors 80 measuring quantities such as:
  room temperature;
  relative humidity;
  the toxic or undesirable gas content in the ambient air (carbon dioxide, ozone, volatile organic compounds, etc.);
  dust, allergens, or other particle content in the ambient air.

As is known, the responses of these sensors 80 are not completely stable over time. It is therefore useful to provide dynamic maintenance to correct their drift. Indeed, a robot that can carry numerous sensors, some of which are networked to render the expected service more robust, may see its services decline or generate false data because of drift in its sensors, which will be integrated into the databases.

To detect drift in a given sensor 80, it is necessary to compare the value it measures to that provided by a reference sensor which is next to it. Traditionally, this involves either a technician visit to the robot deployment site, or sending the robot or its sensor to another test site.

In the context of a network of sensors 80 on board mobile robots, this problem can be alleviated by the presence of reference sensors 40 in the docking station 10 which is presented in this document.

The reference sensors 40 (FIG. 3) may be housed inside the pillar 13 of the docking station. In the example shown in FIGS. 1 and 2, air vents 44, 45 are provided on the pillar 13, on the front and at the top, so that the air measured by the sensors 40 of the docking station 10 is shared with the air measured by the sensors 80 equipping a docked robot 20.

Since all the robots 20 regularly come to a docking station to recharge, they spend a fair amount of time there, allowing enough sampling for comparing data from the onboard sensors 80 and the reference sensors 40. Calculation of drift correction factors and failure detection are performed for each robot which comes to recharge. The maintenance operation consisting of verifying the sensors 80 on board the robots may be done exclusively by means of sensors of the docking station 10.

Figure 10:
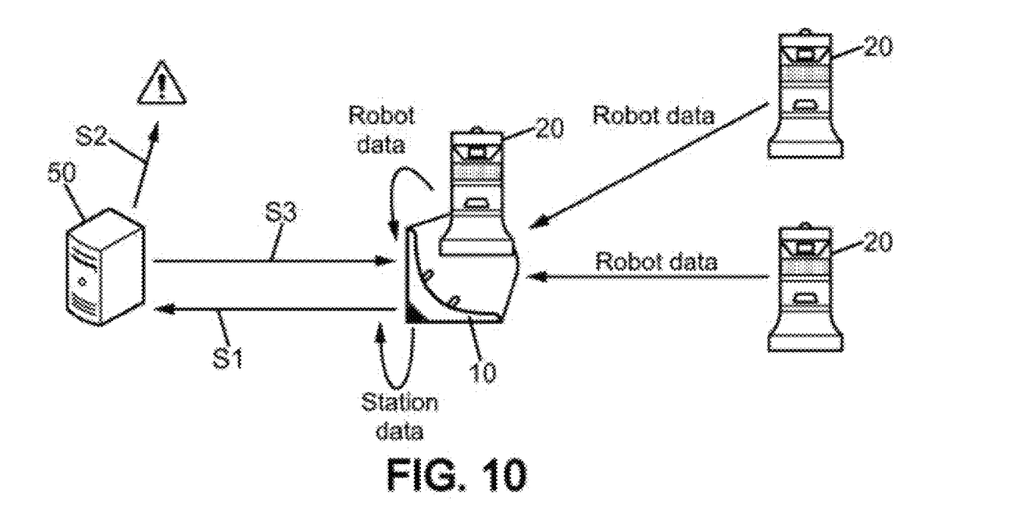
FIG. 10 is a diagram illustrating a mobile robot calibration procedure using the docking station.

Sensor maintenance may for example be performed as follows. The data (raw data and corrected data) measured by the docking station 10 and by the robots 20 are sent to a collection server 50 via the network interface 32 (FIG. 10: step S1). The measured data are analyzed by the server 50 in order to calculate the correction parameters.

The correction calculation for a given sensor 80 of a robot 20, which corresponds to a reference sensor 40 of a docking station 10, may comprise:
 comparing the data measured by the robot 20 located in a docking station 10 (detection by presence of the robot in the station);
 using the value measured by the sensor 40 of the station 10 as a reference;
 estimating the correction from the differences between the measurements made by the docked robot and those made by the station. Depending on the type of sensor, regression which is linear (for example by least squares), polynomial, or other, is applied to the data to define the correction parameters;
 if the drift represented by the correction parameters is too large, an on-site maintenance operation may possibly be decided upon for the sensors 40 of the docking station 80 or for those of a robot (FIG. 10: step S2);
 transmitting the correction parameters to the docking station 10 via the network interface 32 (FIG. 10: step S3) and, from there, to the robots 20 via the WiFi access point 33.

One interesting possibility is to perform a counter-assessment of measurements from the reference sensors 40, using measurements made by sensors of the same type 80 on board a population of robots, applying the principle: "the majority can challenge the reference." In this case, the measurements of the robot sensors 80 are expressed as deviations from the reference measurement from a sensor 40 of the docking station. These deviations given for the different robots of the population are compared. If a majority of the robots confirms a deviation in the same direction, the reference sensor 40 is called into question, and an alert is triggered to the fleet manager so he can decide on a maintenance operation on the reference sensor 40 of the docking station or revalidating the calibration of the reference sensors 40 if this has been done recently.

Making use of the data from the reference sensors 40 equipping the docking station 10 can greatly reduce the need for on-site maintenance for robots 20.

Figure 11:
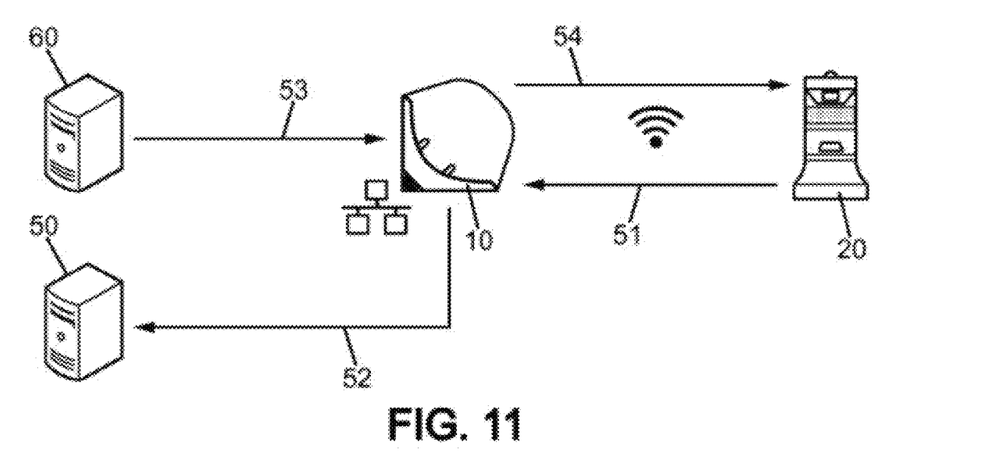
FIG. 11 is a diagram showing an exemplary communication architecture suitable for implementing the invention.

In the context of using a fleet of robots to measure air quality, the data measured by the embedded sensors 80 are continuously sent to the collection server 50 via the WiFi access point 33 of a docking station 10 and its network interface 32 (indicated by arrows 51, 52 in FIG. 11). If necessary, the collection server 50 returns correction parameters to the robots, as has just been described.

The network interface 32 further enables communication with a software update server 60 (FIG. 10) which may be distinct from the collection server 50. When new versions of the robot firmware are developed, they can be downloaded from the update server 60 to the robot 20 via the network interface 32 of the docking station 10 (arrow 53) and its WiFi access point 33 (arrow 54).

On the basis of the features offered by the docking station 10, the proposed architecture again facilitates maintenance, this time of the firmware, of the robot fleet.

The embodiments described above are merely an illustration of the present invention. Various modifications can be made without departing from the scope of the invention as defined in the accompanying claims.

Although the electric power delivery interface equipping a docking station has been described as consisting of a pair of contactors 16, while the electric power receiving interface of a robot has been described as consisting of a pair of charging contacts 28, this is not the only type of power interface that can be used. Induction charging is also possible, for example.

Also note that the technical elements described above concerning the method for guiding the robot to the docking station, the mutual identification of docking stations and robots, the secure management of robot recharging, the communication architecture for robots/docking station/server(s), the procedures for calibrating robot sensors and for updating their firmware, can be implemented independently of one another, although their combination can offer robot users particularly effective docking stations, well suited for the deployment of sizable fleets of robots offering a variety of services.

The invention claimed is:

1. A method for recharging the battery of a mobile robot in an environment, using a docking station located in the environment, the method comprising:
 moving the mobile robot to the docking station;
 emitting a wireless beacon signal from the docking station;
 upon detection of the beacon signal by the mobile robot, making the mobile robot communicate with the docking station such that the docking station retrieves information concerning the mobile robot; and
 initiating the recharging of the battery of the mobile robot in a manner that is dependent on the retrieved information concerning the mobile robot.

2. The method of claim 1, wherein the information retrieved by the docking station concerning the mobile robot comprises an identifier of the mobile robot, the charging beginning if the mobile robot identifier included in the retrieved information corresponds to an identifier in a list of authorized robots stored in the docking station.

3. The method of claim 1, wherein the charge power is selected based on the information retrieved by the docking station concerning the mobile robot.

4. The method of claim 1, comprising:
in response to detection of the beacon signal by the mobile robot, presenting a voltage at an electric power receiving interface comprised in the mobile robot for recharging the battery;
in response to detection of the voltage at an electric power delivery interface comprised in the docking station, transmitting an identification request from the docking station to the mobile robot; and
transmitting information concerning the mobile robot to the docking station in response to the identification request.

5. The method of claim 1, wherein the beacon signal carries an identifier of the docking station, and wherein the mobile robot is prevented from transmitting information concerning the mobile robot when the docking station identifier received in the detected beacon signal does not match any identifier in a list of authorized docking stations stored in the mobile robot.

6. The method of claim 1, further comprising, while recharging the battery of the mobile robot:
monitoring parameters among at least a battery voltage of the mobile robot, a charge current delivered to the mobile robot, and a temperature of a charging circuit of the docking station; and
stopping the charge power when the recharging conditions are no longer met.

7. A robotic equipment comprising:
at least one mobile robot, the mobile robot comprising:
a battery;
a motor system powered by the battery to move the mobile robot within an environment;
an electric power receiving interface for recharging the battery; and
a first communication interface; and
at least one docking station to be placed in the environment, the docking station comprising:
a parking area for receiving at least one mobile robot;
a source of electric power;
an electric power delivery interface for cooperating with the electric power receiving interface of a mobile robot received in the parking area and charging the battery of said mobile robot from the source of electric power;
a source of wireless beacon signal for transmitting a beacon signal around the docking station;
a second communication interface for cooperating with the first communication interface of the mobile robot and retrieving information concerning the mobile robot received in the parking area after emission of the beacon signal by the source of the beacon signal; and
a recharging controller for recharging the battery of the mobile robot received in the parking area in a manner that is dependent on the information concerning the mobile robot received via the second communication interface.

8. A mobile robot docking station comprising:
a parking area for receiving at least one mobile robot in an environment where the docking station is placed;
a source of electric power;
an electric power delivery interface coupled to the source of electric power in order to recharge a battery of a mobile robot received in the parking area;
a source of wireless beacon signal for transmitting a beacon signal around the docking station;
a communication interface for communicating with the mobile robot received in the parking area in order to retrieve information concerning said mobile robot after transmission of the beacon signal by the source of the beacon signal; and
a recharging controller for recharging the battery of the mobile robot received in the parking area in a manner that is dependent on the information concerning said mobile robot retrieved via the communication interface.

9. A mobile robot comprising:
a battery;
a motor system powered by the battery to move the mobile robot within an environment;
an electric power receiving interface for recharging the battery, the power coming from a docking station located in the environment;
a wireless beacon signal detector for detecting a beacon from the docking station;
an interface for communicating with the docking station; and
a controller configured to:
in response to detection of the beacon signal, present a voltage at the electric power receiving interface; and
in response to receiving an identification request via the interface for communicating with the docking station after presenting a voltage to the electric power receiving interface, transmitting identification information concerning the mobile robot to the docking station.

10. The mobile robot of claim 9, wherein the beacon signal carries an identifier of the docking station, the controller is configured not to transmit the mobile robot identification information when the docking station identifier received in the detected beacon signal does not match any identifier in a list of authorized docking stations stored in the mobile robot.

* * * * *